(12) United States Patent
Batz-Sohn et al.

(10) Patent No.: US 7,399,487 B2
(45) Date of Patent: *Jul. 15, 2008

(54) HIGH-CONCENTRATION AQUEOUS DISPERSIONS COMPRISING HYDROPHILIC MICROFINE METAL OXIDE PARTICLES AND DISPERSION AUXILIARIES

(75) Inventors: Christoph Batz-Sohn, Hanau (DE); Petra Brandt, Duisburg (DE); Thomas Dietz, Essen (DE); Steffen Hasenzahl, Hanau (DE); Klaus Jenni, Essen (DE); Kathrin Lehmann, Leverkusen (DE); Ralf Mathiak, Gladbeck (DE); Angela Rüttgerodt, Leverkusen (DE)

(73) Assignee: Goldschmidt GmbH, Essen (DE)

( * ) Notice: Subject to any disclaimer, the term of this patent is extended or adjusted under 35 U.S.C. 154(b) by 768 days.

This patent is subject to a terminal disclaimer.

(21) Appl. No.: 10/456,276

(22) Filed: Jun. 6, 2003

(65) Prior Publication Data

US 2003/0229172 A1    Dec. 11, 2003

(30) Foreign Application Priority Data

Jun. 6, 2002    (DE) .................... 102 25 123

(51) Int. Cl.
    *A61K 9/14*     (2006.01)
    *A61K 9/16*     (2006.01)
    *A61K 33/22*    (2006.01)
    *A01N 59/16*    (2006.01)

(52) U.S. Cl. .................. 424/489; 424/490; 424/641

(58) Field of Classification Search .................. 424/401, 424/489, 490, 641, 642; 514/937
    See application file for complete search history.

(56) References Cited

U.S. PATENT DOCUMENTS 4,138,477 A * 2/1979 Gaffar ..................... 424/52

FOREIGN PATENT DOCUMENTS

DE      3941543 A1      12/1989
GB      2206339 A       1/1989
WO      WO 90/06103     6/1990

* cited by examiner

*Primary Examiner*—Johann Richter
*Assistant Examiner*—Konata M George
(74) *Attorney, Agent, or Firm*—Scully, Scott, Murphy & Presser, P.C.

(57) ABSTRACT

Aqueous dispersions comprising microfine metal oxide particles and dispersion auxiliaries, wherein, as dispersion auxiliaries, at least one of the compounds of the general formula (I)

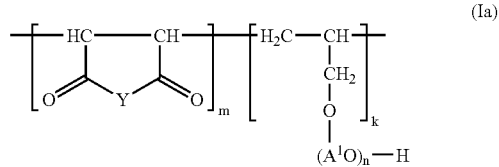

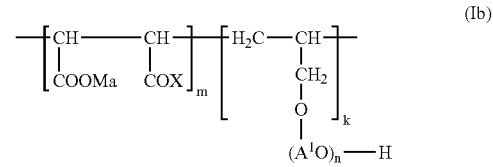

in which
M is hydrogen, monovalent or divalent metal cation, ammonium ion, organic amine radical;
a is 1, or where M is a divalent metal cation, is ½;
X is likewise —$OM_a$ or —O—$(C_pH_{2p}O)_q$—$R^1$ where $R^1$=H, aliphatic hydrocarbon radical having 1-20 carbon atoms, cycloaliphatic hydrocarbon radical having 5 to 8 carbon atoms, optionally substituted aryl radical having 6 to 14 carbon atoms, p=2 to 4, q=0 to 100, —$NHR^2$ and/or —$NR^2_2$ where $R^2$=$R^1$ or —CO—$NH_2$;
Y is O, $NR^2$;
$A^1$ is ethylene radical, propylene radical, isopropylene radical, butylene radical;
m is 10 to 30;
n is 0 to 50; and
k is 10 to 30, where the sum m+k is in the range from 20 to 60, is co-used.

9 Claims, 1 Drawing Sheet

HIGH-CONCENTRATION AQUEOUS DISPERSIONS COMPRISING HYDROPHILIC MICROFINE METAL OXIDE PARTICLES AND DISPERSION AUXILIARIES

DESCRIPTION

1. Field of the Invention

The present invention relates to aqueous dispersions comprising hydrophilic microfine metal oxide particles and, as dispersion auxiliaries, maleic anhydride/maleate-acrylate copolymers. The present invention also relates to the use of these dispersions for the preparation of cosmetic formulations, in particular sunscreen formulations.

2. Background of the Invention

To protect skin against over-intensive UV radiation, cosmetic preparations, such as creams or lotions, containing UV filters are used which are largely transparent and pleasant to use on the skin.

UV filters comprise one or more organic compounds which absorb in the wavelength range between 290 and 400 nm: UVB radiation (290 to 320 nm); UVA radiation (320 to 400 nm).

The higher-energy UVB radiation causes typical sunburn symptoms and is also responsible for suppressing the immune defence, while UVA radiation, which penetrates more deeply into the layers of skin, causes premature aging of the skin. Since the combined effect of the two types of radiation is said to favor the formation of light-induced skin cancer diseases such as skin cancer, the search for ways of significantly improving the UV protection has been ongoing for many years.

It has been found that microfine (ultrafine) pigments based on metal oxides can also scatter, reflect and absorb UV radiation. Highly-dispersed formulations containing microfine pigments based on metal oxides represent an effective addition to organic UV filters in sunscreen compositions.

Microfine titanium dioxide is used widely in cosmetic formulations since it is chemically inert, toxicologically safe and leads neither to skin irritations nor to sensitization. Microfine titanium dioxide is the currently most used and most important mineral light protection substance. In addition to titanium dioxide, microfine zinc oxide is used to an increasing degree.

A distinction is made between coarsely divided material (pigment) and finely divided material (micropigment). For the micropigments, the average primary particle size is usually significantly less than 200 nm, mostly in the range from 10 to 100 nm, usually less than 50 nm.

The coarsely divided pigment (0.2 to 0.5 µm) absorbs or reflects broadly and relatively consistently over the entire UV region and the visible light region, while the finely divided material exhibits a significant increase in activity in the UV region with a simultaneous loss of activity in the long-wave UVA and, in particular in the visible, region. Since only a little visible light is reflected, preparations based on this active ingredient are largely transparent.

Due to their particularly large specific surface areas, microfine $TiO_2$ particles are photoactive and are able to generate reactive species (e.g., hydroxyl radicals). For use in cosmetic compositions, it is therefore necessary to suppress the photochemical activity of microfine $TiO_2$ particles. This is achieved by inorganic and organic surface components, such as, for example, $Al_2O_3$, $SiO_2$ and/or fatty acid (salts), and siloxanes. These substances can adhere to the surface by chemisorption or physisorption (lattice doping/coating). Chemisorption leads to grades which are suitable for cosmetic light protection agents.

The primary particles of microfine titanium dioxide are not present in the dry pigment powder in isolated form, but rather form aggregates and agglomerates.

Primary particles refer to the smallest particles which are formed during the preparation of the pigments. Primary particles can be in the form of individual crystallites or in the form of two or more crystallites which have intergrown tightly with one another along faces. Aggregates refer to particles composed of two or more primary particles, in which the primary particles are intergrown with one another along faces. Agglomerate is understood as meaning an association of primary particles or aggregates that are held together via attractive forces, such as, for example, hydrogen bridge bonds.

Agglomerates are present in every pigment powder, but are undesired in cosmetic transparent formulations since they can be identified as particles on the skin, often times with the naked eye. Moreover, agglomerates in cosmetic formulations reduce the transparency of the formulation as well as the UV protective action of a sunscreen composition and settle out during storage. Agglomerates therefore have to be largely comminuted again.

The entire process of incorporation, comminution and simultaneous distribution of solids in a liquid phase is referred to as dispersion.

As the primary particle size decreases, the specific surface area increases, as does the active area for the formation of aggregates and agglomerates, and also for adsorption processes. A result of the foregoing is that the stability of the emulsion can be endangered.

The comminution of the agglomerates and wetting of the newly provided surfaces is only possible with the aid of high shear forces and is carried out in practice in a large number of different special machines, such as, in particular, dissolvers and ball mills.

In practice, it has been found that as the finely divided nature of the particles increases, so too do the dispersion problems, with the result that the dispersion process overall represents one of the most complex sub-steps in the preparation of cosmetic formulations.

The requirements of practice therefore involve separating the most complex part of the dispersion—the comminution of the agglomerates—from the preparation of the actual cosmetic formulations, and preparing stable aqueous dispersions with the highest possible content of microfine $TiO_2$ which preferably have a low-viscosity or at least are pumpable or flowable.

A large number of proposals have been made which aim to solve this problem.

British Patent GB-A-2 206 339 describes dispersions of titanium dioxide particles of particle size from 0.01 to 0.15 µ in organic oils and dispersion auxiliaries based on polyesters, salts of hydroxycarboxylic acids and/or hydroxyl-group-free $C_{6-22}$-fatty acids or salts thereof, as well as the use thereof as sunscreens.

WO-A-90/06103 proposes to reduce the clumping tendency (tendency for reagglomeration of titanium dioxide particles with particle sizes <100 nm) through coatings made of phospholipids.

DE-A-39 41 543 describes a process for the preparation of aqueous dispersions of needle-like finely divided titanium dioxide that is optionally coated with hydrous metal oxides, by grinding the titanium dioxide particles in the presence of a polycarboxylic acid or salt thereof as dispersant, and the use as sunscreens.

Although these dispersions have tendential improvements, the prior art dispersions still have the disadvantage that the aqueous dispersions comprise insufficiently high contents of microfine TiO$_2$, sediment during storage and/or the photoactivity is still too high.

A further significant disadvantage is that the prior art dispersions are not stable in the pH range from about 5 to 7 (i.e., the pH of the surface of skin) which is particularly preferred for cosmetic formulations.

An object of the present invention is to overcome the existing disadvantages and to prepare stable, high-concentration, aqueous dispersions of microfine metal oxide particles, in particular microfine titanium dioxide, with comparatively low viscosities, which are also stable in the acidic physiologically favorable pH range.

SUMMARY OF THE INVENTION

The aforementioned object is achieved in the present invention through the use of uncoated or hydrophilically coated microfine metal oxide particles and maleic anhydride/maleate-acrylate copolymers as dispersion auxiliaries.

The present invention therefore provides aqueous dispersions comprising:
A) uncoated and/or hydrophilically coated microfine metal oxide particles and, as dispersion auxiliaries,
B) at least one of the compounds of the general formula (I)

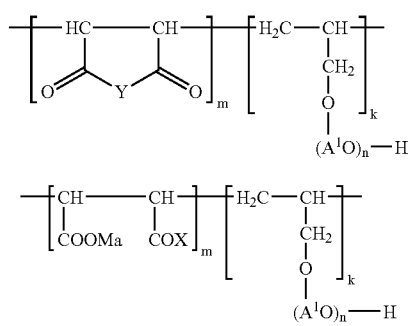

in which
M is hydrogen, a monovalent or divalent metal cation, an ammonium ion, or an organic amine radical;
a is 1, or where M is a divalent metal cation, a is ½;
X is —OM$_a$ or —O—(C$_p$H$_{2p}$O)$_q$—R$^1$ where R$^1$=H, an aliphatic hydrocarbon radical having 1-20 carbon atoms, a cycloaliphatic hydrocarbon radical having 5 to 8 carbon atoms, an optionally substituted aryl radical having 6 to 14 carbon atoms, p=2 to 4, q=0 to 100, —NHR$^2$ and/or —NR$^2$$_2$ where R$^2$=R$^1$ or —CO—NH$_2$;
Y is O, or NR$^2$;
A$^1$ is an ethylene radical, a propylene radical, an isopropylene radical, or a butylene radical;
m is 10 to 30;
n is 0 to 50; and
k is 10 to 30, where the sum
m+k is in the range from 20 to 60, preferably from 20 to 40, and optionally
C) further auxiliaries and additives, and
D) water.

The present invention further provides for the use of the above-mentioned aqueous dispersions for the preparation of cosmetic formulations.

BRIEF DESCRIPTION OF THE DRAWINGS

The sole FIGURE is a plot of Zeta potential [mV] or specific conductivity vs. pH for the formulation of Example 2 of the present invention.

DETAILED DESCRIPTION OF THE INVENTION

Figure 1:
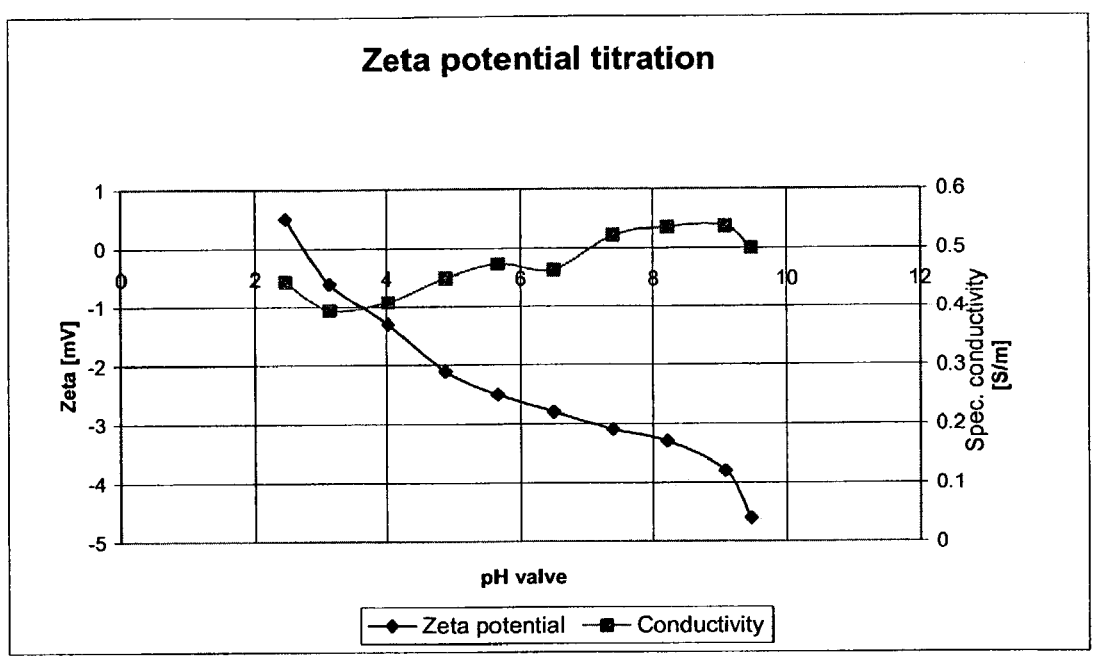

In the compounds of general formula I used according to the present invention

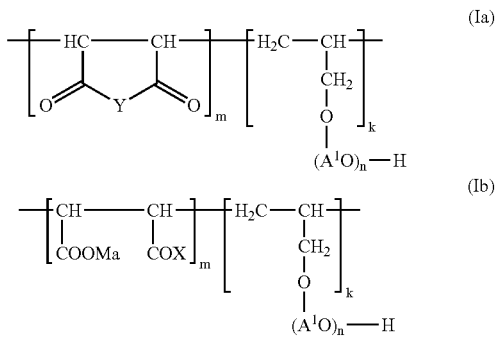

in which
A$^1$ is an ethylene radical, a propylene radical, an isopropylene radical, or butylene radical;
m is 10 to 30;
n is 0 to 50;and
k 10 to 30, where the sum
m+k is in the range from 20 to 60, preferably from 20 to 40,
—(A$^1$O)$_a$—is either a homopolymer of one of the alkylene oxides, or block copolymers or copolymers with random distribution of two or more of the monomers within the polymer molecule,
the units
[ ]$_m$ and [ ]$_k$ can likewise be present as block copolymers or copolymers with random distribution of two or more of the monomers within the polymer molecule.

These products are used in amounts from 0.5 to 40% by weight, preferably in amounts from 1 to 35% by weight, based on the aqueous dispersion.

Microfine metal oxide particles which can be used in the present invention are, in principle, all metal oxides that are customary in the respective fields of use. The term "microfine" or "ultrafine" is used herein to denote particle sizes of, on average, <about 250 nm, preferably to about 100 nm and below. For use in cosmetic formulations, the choice is naturally limited to compounds that are safe from a toxicological and dermatological point of view, such as, cerium oxide, zinc oxide, iron oxide and, in particular, titanium dioxide.

The microfine metal oxide particles used according to the present invention are standard commercial products that are obtainable under the respective trade names, also with inorganic or organic coatings, such as, for example, Micro Titanium Dioxide MT 100 AQ and MT 150 W (Tri-K-Tayca), UV-Titan M 212 (Kemira) and titanium dioxide P-25 (Degussa).

According to the present invention, preference is given to titanium dioxide having an average primary particle size of < about 250 nm, preferably <100 nm and, in particular, in the range from 10 to 100, which can optionally be coated with aluminum oxide and/or glycerol or silica and/or glycerol or any comparable hydrophilic inorganic substance.

Titanium dioxide P-25 (Degussa) has proven particularly advantageous in the present invention. Titanium dioxide P-25 consists, in crystallographic terms, of about 80% anatase and about 20% rutile and has a primary particle size of about 21 nm. Titanium dioxide P-25 is characterized as having a high cosmetic acceptance and very good water resistance.

In addition to the above mentioned components, further auxiliaries and additives known in this field can be co-used as desired. Illustrative examples of such auxiliaries and addivitives include, but are not limited to: ethanol, propanol, butanol, propylene glycol, butylene glycol, pentylene glycol, hexylene glycol, alkoxylates, glycol ethers, glycols, polyethylene glycols, polypropylene glycols, polybutylene glycols, glycerol ester ethoxylates, glycerol, polyglycerol, sorbitol, sucrose, fructose, galactose, mannose, polysorbate, starch, xanthan gum, carrageenan gum, cellulose derivatives, alginates, glycol esters, sorbitan esters, opacifiers, solubilizers, ethoxylated fatty alcohols, sodium chloride, sodium sulfate, magnesium sulfate, buffer systems, cholesterol, pantothenic acid, ascorbic acid, polyacrylic acids, and carbomers.

The dispersions according to the present invention are preferably used for the preparation of cosmetic formulations, such as foundation, colored powders, lipstick, hair colorants, day creams and, in particular, sunscreen preparations. The dispersions can be in the customary forms, such as, for example, W/O or O/W dispersions (emulsions), gels, creams, lotions, sprays.

The resulting dispersions of the present invention are characterized by a high finely divided nature of dispersed solid, long-term storage stability and low viscosity.

The viscosity is measured using a Brookfield RVT, spindle 5, in accordance with the manufacturer's instructions and is, at room temperature at 10 revolutions per minute (rpm), between 10 and 40,000 mPas.

In order to stabilize the finely divided state of distribution achieved by the dispersion, reagglomeration must be suppressed in the long term. This is achieved by adding dispersion additives, as the compound of the formula I shows.

The zeta potential can be used as a characteristic of the electrostatic stabilization of a dispersion. The zeta potential is the outwardly effective potential of the particle and represents a measure of the electrostatic interaction between individual particles. Zeta potential plays a role in the stabilization of suspensions and, in particular, of dispersions with dispersed microfine particles. At a zeta potential value of $<-20$ mV or $>+20$ mV, there is strong repulsion between the particles; the dispersions remain stable. At values within this range, the repulsion becomes so low that the van der Waals' forces permit the formation of agglomerates, leading to undesired sedimentation of the particles.

The sole FIGURE of the present invention shows a plot of Zeta potential (left hand y-axis) vs. pH for the formulation of Example 2. The sole FIGURE also includes a plot of specific conductivity (right hand y-axis) vs. pH of the same formulation.

Measurements of the aqueous dispersions according to the present invention have revealed a significantly lower zeta potential in the pH range from about 3 to about 10.

Surprisingly, it has now been found that the dispersions obtained according to the present invention are storage-stable at room temperature for longer than 6 months and at 50° C. for longer than one month.

The dispersions according to the present invention can be prepared by methods generally known in this field, the mixing devices used being automatic dispersers with toothed discs, bead mills, rotor-stator systems, or Scandex shakers.

In an expedient manner, the dispersion additives and optionally co-used polyols are introduced into water, and the pigment is sprinkled in with appropriate stirring. The predispersion obtained in this way is then finely dispersed.

The aqueous dispersions comprise:
5 to 80% by weight of component A), in particular 20 to 60%, 0.5 to 30% by weight of component B), in particular 3 to 15%, 0 to 30% by weight of component C), in particular 1 to 10%, ad 100% by weight of water.

Auxiliaries and additives which may be co-used are glycerol, propylene glycol, butylene glycol and higher glycol, polyglycerols, sorbitol and comparable sugar alcohols, and 0.1 to 0.5% of water-soluble or water-dispersible preservatives.

The following examples illustrate formulations of the present invention which are made using the method and components described herein above.

Examples 1 to 4

| Example | 1 | 2 | 3 | 4 |
|---|---|---|---|---|
| TiO$_2$ (Degussa P 25) | 35.0% | 35.0% | 40.0% | 40.0% |
| Compound of the formula I (MW 15000) | 10.5% | 10.5% | 12.0% | 12.0% |
| Glycerol | — | 10.0% | — | 5.0% |
| Propylene glycol | — | — | 10.0% | — |
| Water | 54.5% | 44.5% | 38.0% | 43.0% |
| Viscosity (mPas) | 105 | 131 | 5000 | 9000 |

While the present invention has been particularly shown and described with respect to preferred embodiments thereof, it will be understood by those skilled in the art that the foregoing and other changes in form and detail may be made without departing from the spirit and scope of the present invention. It is therefore intended that the present invention not be limited to the exact forms and details described and illustrated, but fall within the scope of the appended claims.

What is claimed is:
1. An aqueous dispersion comprising:
A) uncoated or hydrophilically coated microfine metal oxide particles; and
B) at least one compound of general formula (Ia) or (Ib)

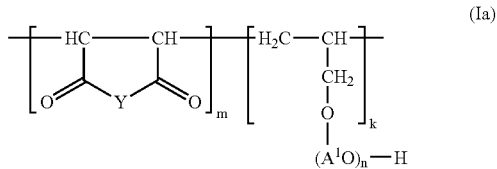
(Ia)

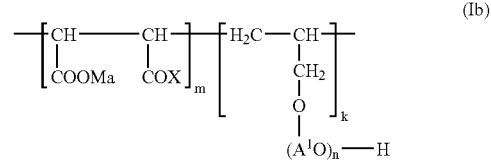
(Ib)

in which

M is hydrogen, a monovalent or divalent metal cation, or an ammonium ion;

a is 1, or where M is a divalent metal cation, a is ½;

X is $OM_a$ or $-O-(C_pH_{2p}O)_q-R^1$ where $R^1$=H, an aliphatic hydrocarbon radical having 1-20 carbon atoms, a cycloaliphatic hydrocarbon radical having 5 to 8 carbon atoms, an optionally substituted aryl radical having 6 to 14 carbon atoms, p=2 to 4, q=0 to 100, $-NHR^2$ and/or $NR^2_2$ where $R^2=R^1$ or $-CO-NH_2$;

Y is O, or $NR^2$;

$A^1$ is an ethylene radical, a propylene radical, an isopropylene radical, or a butylene radical;

m is 10 to 30;

n is 0 to 50; and k is 10 to 30, where the sum m +k is in the range from 20 to 60.

2. The aqueous dispersion of claim 1 wherein the dispersion comprises 20 to 60% by weight of said microfine metal oxide particles.

3. The aqueous dispersion of claim 1 wherein the microfine metal oxide particles comprise zinc oxide, titanium dioxide or a mixture thereof that are hydrophilically coated with aluminum oxide/glycerol or silica/glycerol.

4. The aqueous dispersion of claim 1 wherein the microfine metal oxide particles comprise uncoated zinc oxide, uncoated titanium dioxide or a mixture thereof.

5. The aqueous dispersion of claim 1 wherein the metal oxide particles have a primary particle size of between 10 and 100 nm.

6. The aqueous dispersion of claim 1 wherein compounds in which $A^1$ is an ethylene radical, m is 10 to 30, n is 5 to 20, k is 10 to 30 and where the sum m+k is in the range from 20 to 40.

7. The aqueous dispersion of claim 1 wherein the dispersion has a measured viscosity between 10 and 40,000 mPas at room temperature.

8. The aqueous dispersion of claim 1 further comprising cosmetic auxiliaries and cosmetic additives.

9. A cosmetic formulation comprising the aqueous dispersion of claim 1.

* * * * *